United States Patent [19]

Stenström et al.

[11] Patent Number: 4,816,231
[45] Date of Patent: Mar. 28, 1989

[54] HEAT TREATING CASSETTE FOR A CONVEYOR APPARATUS

[75] Inventors: Lennart Stenström, Huddinge; Lennart Wahlström, Tumba; Björn Lindström, Stockholm, all of Sweden

[73] Assignee: Alfastar AB, Sweden

[21] Appl. No.: 929,106

[22] PCT Filed: Feb. 14, 1986

[86] PCT No.: PCT/SE86/00062
  § 371 Date: Oct. 17, 1986
  § 102(e) Date: Oct. 17, 1986

[87] PCT Pub. No.: WO86/04787
  PCT Pub. Date: Aug. 28, 1986

[30] Foreign Application Priority Data

Feb. 18, 1985 [SE] Sweden .................................. 8500752

[51] Int. Cl.⁴ .................................................. A61L 2/02
[52] U.S. Cl. ...................................... 422/300; 422/292; 422/304; 198/803.14
[58] Field of Search ............... 422/292, 295, 297, 300, 422/302–304; 198/803.14; 99/359–367, 369–371

[56] References Cited

U.S. PATENT DOCUMENTS

| | | | |
|---|---|---|---|
| 3,970,188 | 7/1976 | Smorenburg | 198/803.14 |
| 4,385,035 | 5/1983 | Akitoshi et al. | 422/297 |
| 4,541,992 | 9/1985 | Jerge et al. | 422/300 |
| 4,547,343 | 10/1985 | Takano et al. | 422/302 |

FOREIGN PATENT DOCUMENTS 83385  7/1983  European Pat. Off. .

Primary Examiner—Barry S. Richman
Assistant Examiner—Jill Johnston
Attorney, Agent, or Firm—Wegner & Bretschneider

[57] ABSTRACT

A cassette to be used in a conveyor device for products, for instance food stuff. The cassette (18) comprises a thin, broad-sided and broken through casing of substantially uniform thickness having an openable cover of broken through type. The casing and cover are interconnected along one side of the cover in several joints (47) and are interconnectable at several locking locations (48) along an opposite side of the cassette such that the casing and cassette in spite of the broken through structure, form a rigid and strong unit when the cover is closed.

10 Claims, 5 Drawing Sheets

HEAT TREATING CASSETTE FOR A CONVEYOR APPARATUS

FIELD OF THE INVENTION

The present invention relates to a cassette in a transport device for products which are to be processed by heat treatment under well controllable forms. Products of specific interest in this context are such that require heat stabilization for obtaining an extended shelf-life, for instance food products or pharmaceutical compositions.

The term heat stabilization is thought to involve a number of general processes as sterilization, pasteurization, cooling, etc.

The type of heat stabilization thought of at a first hand in this context comprises known concepts for refining and improving the efficiency of general processes.

BACKGROUND OF THE INVENTION

In the stabilization process there for instance may be included a method for a fast pre-heating to a temperature distribution in the product suited for a microwave treatment. A two-step process comprising a contact with a hot medium directly followed by a contact with a cooler medium does in this case precede the microwave treatment.

It is also possible to adjust the temperature profile in advance such that the microwave treatment gives a uniform temperature profile within the product.

A further possibility is to carry out the microwave treatment in water or other liquid and in such case control the water temperature so that the tendency of increased surface temperature is suppressed.

A heat stabilization according to the present concept implies a qualified process technology and it is of utmost importance that the physical conditions for the stabilization/process are the proper ones.

The problem of the invention is to provide a device that allows a sophisticated process handling of products packed in a flexible packaging material. It should for instance be prevented that the product dissipates vapour and expands (blows up) and it is also necessary to transport the product into and out from a pressurized zone. Furtheron, it is of importance to get a uniform, fast heating whereby a uniform maximum thickness of the product is especially important for products lacking specific form as stews and for products that tend to change their form when heat treated, for instance slices of meat. It is also of importance that the end product obtained in the system is a product which is suited for rational packaging and cartonning systems.

OBJECT OF THE INVENTION

The object of the invention is to offer a cassette which surrounds the product and meets the several requirements according to the definition of the problem.

SUMMARY OF THE INVENTION

The invention provides a cassette to be used in a conveyor device for products, preferably food stuff and pharmaceutical compositions, which are to be heat stabilized. The cassette is distinguished by comprising a thin, broad-sided and broken through casing having an openable cover of a broken through type, and in that the casing and cover are interconnected at a plurality of hinge locations along one side of the cassette adn are connectable to each other at a plurality of locking locations along one opposite side of the cassette such that the casing and cover, in spite of the broken through structure, forms a rigid and strong unit when the cover is closed.

In one embodiment of the invention the casing and cover comprise a network of thin ribs.

In one embodiment the cover is shearable in the plane thereof and hook-shaped elements on the cover are engageable with the casing.

In another embodiment of the invention the cover is shearable and hook-shaped elements on the casing are engageable with the cover.

The hook-shaped elements preferably are arranged to grip around locking shoulders of the casing or cover.

Preferably each one of the hook-shaped elements has a cut out which surrounds a substantial part of the locking shoulder.

In another embodiment of the invention the cover is locked at a plurality of locking locations by a slider.

Preferably the cassette is such that the sides thereof in the transport direction are solid and provided with ears which allow the cassettes to be joined into a strain resistant, pivoted chain.

Preferably the ears are round such that they may be accomodated in recesses formed in flaps of a sluice of the turnstile type or a device having a passageway which includes moveable flaps to bar passage, by means of which a chain of cassettes may be brought into and out from an over-pressure zone.

Opposite guide and drive pins are arranged on the sides of the cassette in the transport direction such that they guide the cassettes of the cassette chain in guide rails arranged along the transport path of the cassette chain and drive the cassettes together with driving means, for instance arranged in the sluice.

SPECIFIC DESCRIPTION

Figure 1:
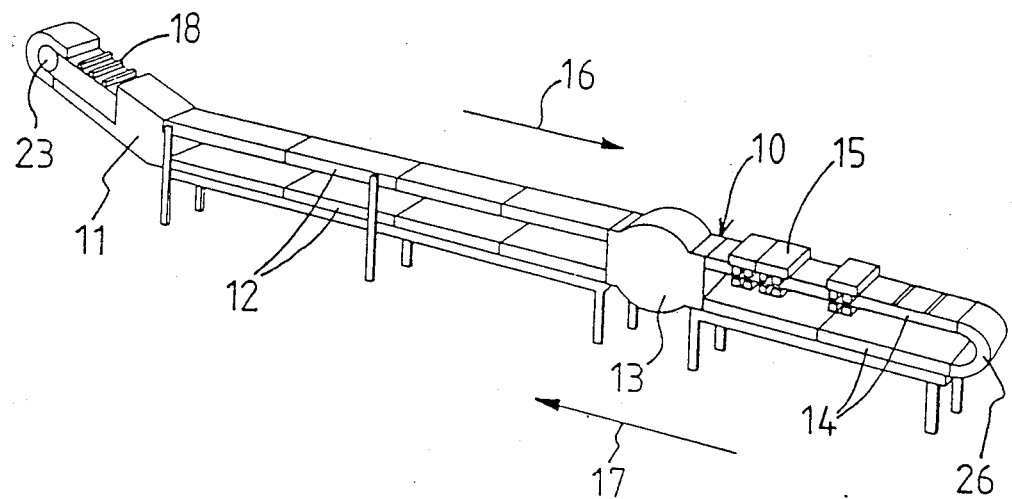
FIG. 1 in a perspective view shows an example of a heat stabilization line where the cassette according to the invention is included, FIG. 2 in a perspective view shows another example of a line where the invention idea is realized, FIG. 3 in a perspective view shows a first type of a module for forming a part of a confinement in which cassettes according to the invention are arranged.

In FIG. 1 the reference numeral 10 generally represents a heat stabilization system comprising an input and output unit 11, module units 12 of the low pressure type arranged at two levels above each other, a sluice device 13 and high pressure module units 14 arranged above each other. Some of the latter modules are provided with microwave applicators 15 if necessary at both levels.

The module units 12 and 14 basically comprise straight elements of equal length which if necessary may have angled connection flanges for obtaining for instance a bump in the path, and when the units are interconnected into a system, for instance according to FIG. 1, there is formed a first processing path generally in a direction 16 and a second path in the opposite direction 17.

In FIG. 1 such paths are parallel and located right above each other, but it is of course possible to displace the paths and the bumps, etc. laterally. The term "bumps" when used in the art means a conveyor path having an extension which is not of a single plane. In other words, "bumps" in a conveyor path refers to a extension whereby adjacent modules form an upward slope directly followed by a downward slope.

Figure 8:
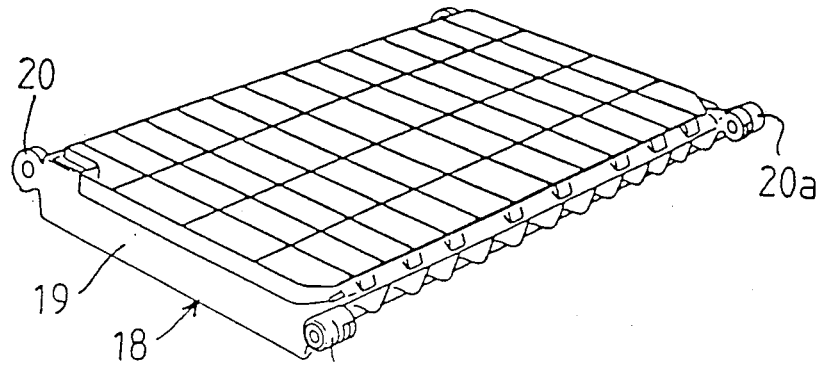
Figure 11:
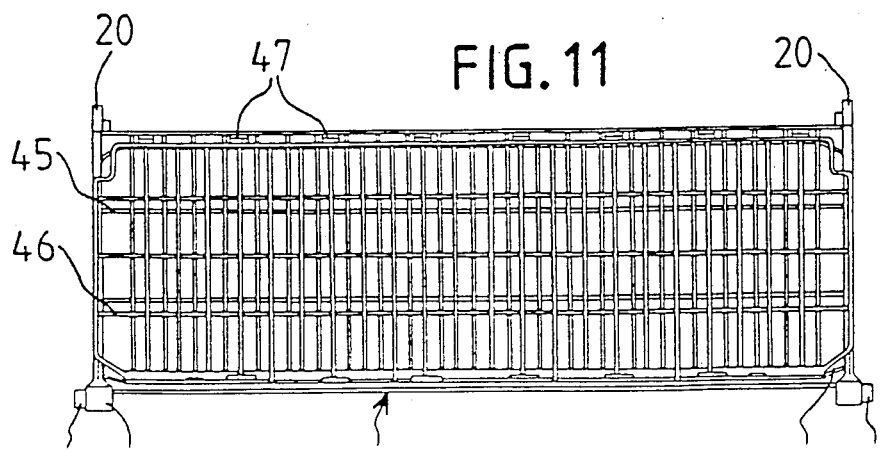

The module units form a confinement for a conveyor system comprising cassettes 18 (FIGS. 8 and 11). At the input and output unit 11 the conveyor system is not confined meaning that the interconnected cassettes 18 are visible (in FIG. 1 the cassettes have been shown with upright covers, and in FIG. 2 the covers are closed). The cassettes form the means for surrounding the product. The side pieces 19 (FIG. 8) of the cassette are formed as links comprising link element 20, 20a at each corner thereof and dogs 21 for co-operation with driving members in the sluice. Driving members 23, 27 for co-operation with the dog members may alternatively be arranged in the input and output unit 11 or in the turn around module (26 in FIG. 4a).

In the present case active processing portions of the conveyor are arranged at both sides of the sluice 13, but it is of course also possible to use such conveyor portions only at one side of the sluice.

Figure 2:
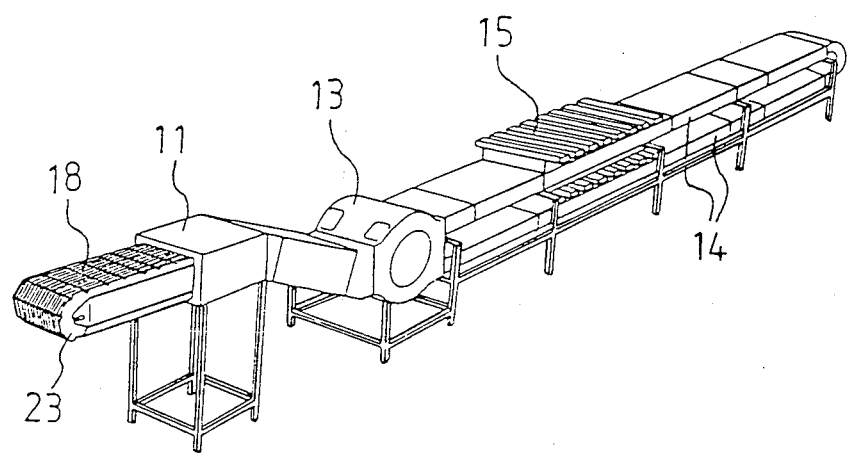

FIG. 2 for instance shows an embodiment where the input unit 11 is directly connected to the sluice.

The module units 12, 14 basically have the same exterior dimension and size, respectively, but they may be dimensioned for different pressures and may be supplemented by insulation of different thicknesses depending on the process specification and the specific type of system chosen.

The idea of using module units as a confinement for instance allows the product to be fully or partially encompassed by a fluid, preferably in a liquid phase and flowing (water). It is also possible to provide a module unit with a restriction for forming a "mini sluice" (see 22 in FIG. 3a), the purpose of which is to delimit specific treatment zones in excess to what will be obtained by the actual sluice.

The length of one module unit is selected such that the double module length corresponds to an integral number multiple of the length of the cassette 18, meaning that the operative length of the process line will be easily adjustable by mounting/demounting a number of module units and cassettes, respectively, having the said length ratio.

Figure 3:
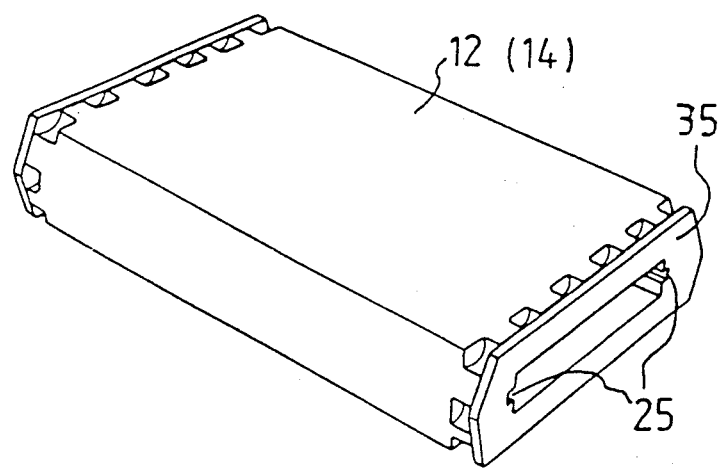
FIG. 3a shows a modified type of a module unit according to FIG. 3.
Figure 3A:
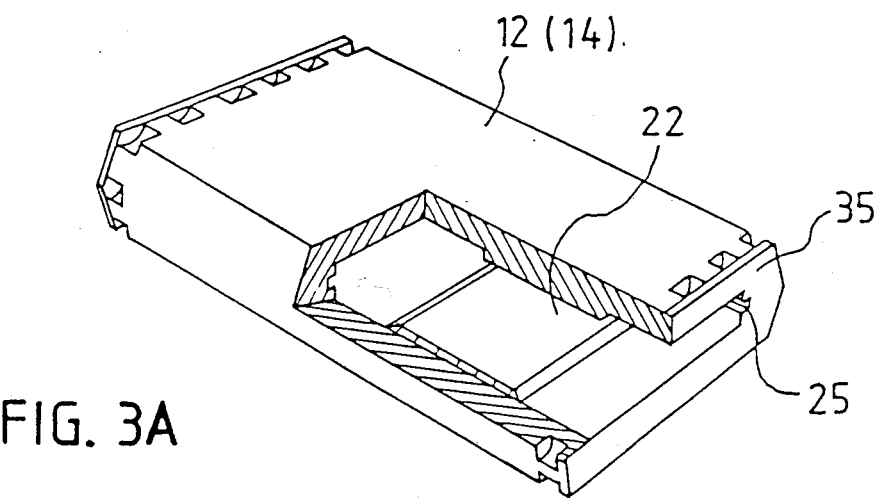

The module unit 12 (14) in FIG. 3 and 3a, respectively, basically has an internal cross section defined by the shape of the cassette and the desired environment in the actual section. The reference numeral 22 in FIG. 3a denotes a restriction, for instance for acting as a partition between environments of for instance different temperatures, flow rates or pressures.

Means 24 for individual temperature sensing in the product may be arranged in each module unit 12, 14, 30, 32.

The longitudinal internal grooves 25 are guide grooves in which the pins 24 of the cassettes ride.

Figure 4:
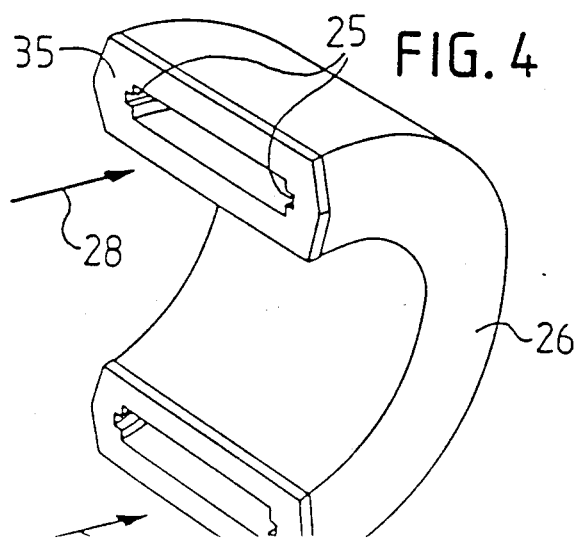
FIG. 4 in a perspective view shows another type of module unit, a so called turn around unit.
Figure 4A:
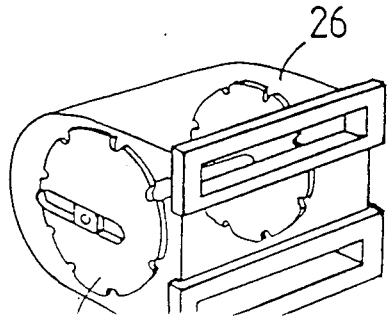
FIG. 4a shows another type of turn around unit, FIG. 5 in a perspective view shows a connection housing, FIG. 6 in a perspective view shows a microwave module, FIG. 7 in a perspective view shows a microwave applicator, FIG. 8 in a perspective view shows a product cassette according to the invention representing the elements of which the conveyor according to the invention is built up.

In FIG. 4 there is shown a turn around unit 26 which reverses the conveyor from the forwards direction 16 to the return direction 17. The unit has guide grooves 25 for the conveyor but it is also possible, as appears from FIG. 4a, to use a free-running wheel 27 (FIG. 4a) gripping the conveyor in order to reverse the transport direction. Similar wheels may be used for driving in the input module 11.

In order to facilitate the reversing operation without unnecessary friction and wearage it is of advantage if water or other fluid flows in a direction towards the turn around or reversing module in the direction of the arrows 28, 29. The flow contributes to the placement of the conveyor into a "natural loop-form" in the forward direction and the return direction, respectively, meaning that the friction forces are reduced.

Figure 5:
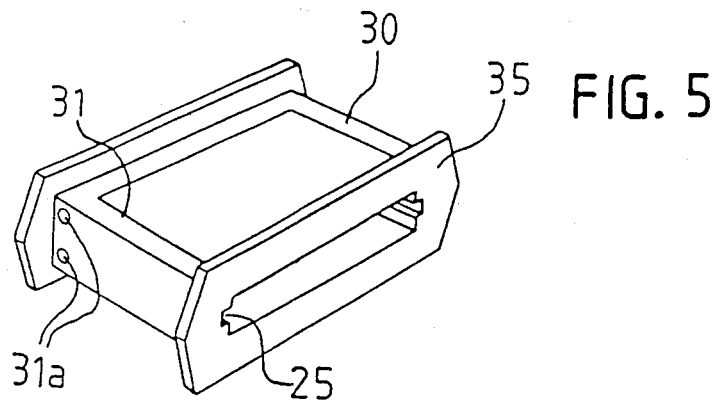

In FIG. 5 there is shown a module unit formed as a connection housing 30 to be inserted in a desired position in the line for allowing connection of a conduit for the actual fluid, for instance water, vapour or air, to the process active interior of such module unit. The connection is obtained for instance through openings 31a. The interior of the housing 30 is available through an opening 31 which normally is closed by a cover which also may be a seat for connections and for instance devices for temperature measurement.

Figure 6:
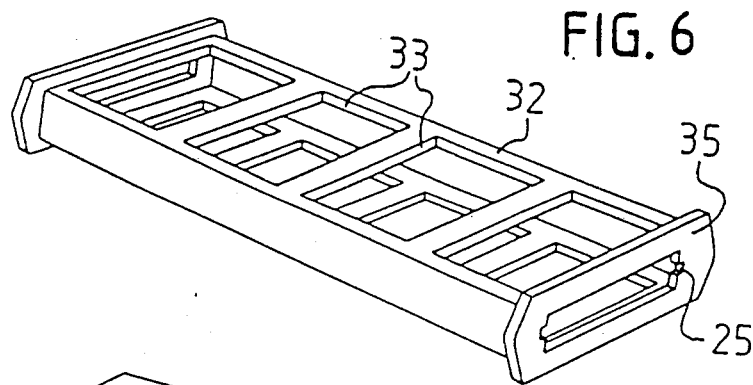
Figure 7:
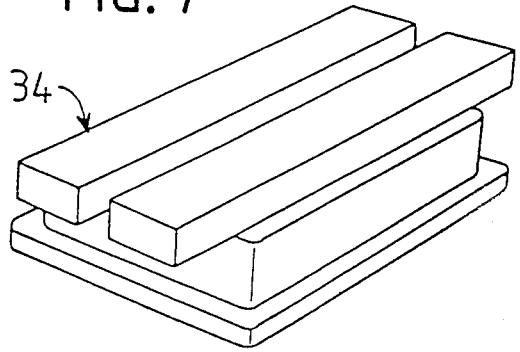

In FIG. 6 there is shown a microwave module 32 having openings 33 for mounting microwave applicators 34 (FIG. 7).

All module units 12, 14, 30, 32 have a length which is related to the length of the cassette 18 such that the double module length is an integral number multiple of the length of the cassette. The module units are provided with flanges 35 which if necessary may be somewhat angled from the perpendicular connection plane of a respective module.

Figure 9:
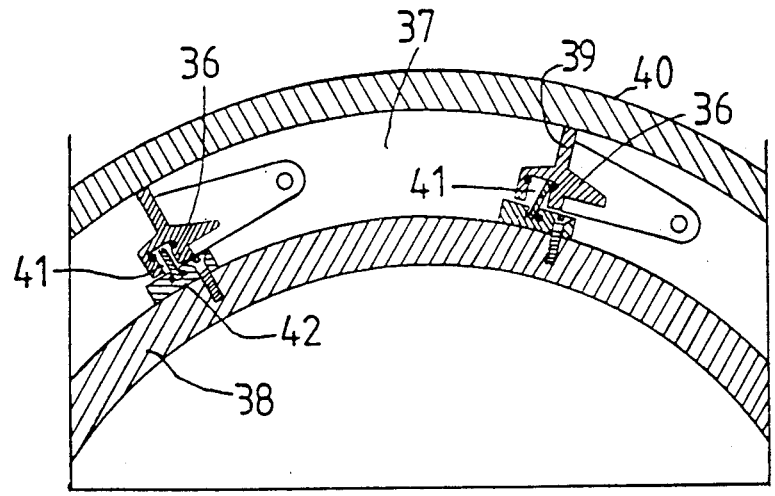
FIG. 9 is a radial partial section through the sluice.
Figure 10:
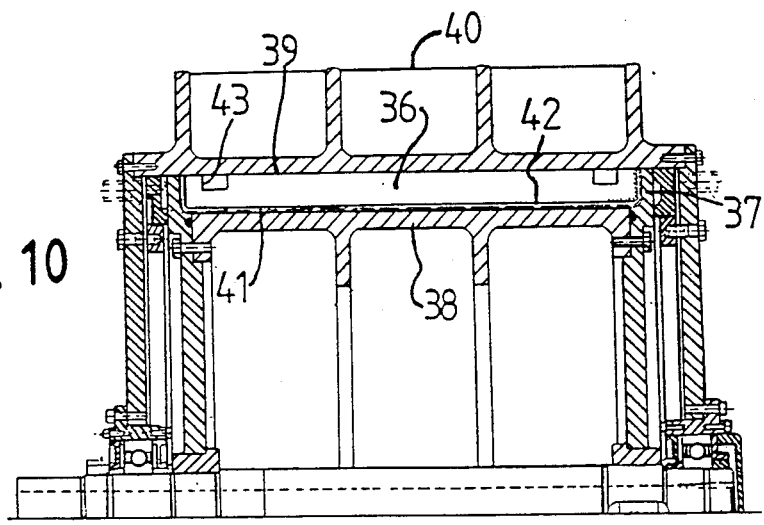
FIG. 10 is an axial partial section through the sluice, FIG. 11 in a more complete view from above shows a cassette device according to the invention.

In FIGS. 9 and 10 there is shown an embodiment of a sluice 13 having radially displaceable flaps 36. Such flaps are journalled in a flange 37 on the drum 38 and are uniformally distributed around the periphery of the drum.

Each flap 36 has a radially outer sealing portion 39 for abutment against the inside of the housing 40. It may be necessary to add a material having a low friction and being wear resistant in the region of the outer sealing.

At the side of each flap 36 facing the drum there is a longitudinal groove 41 extending in the direction of the generatrix of the drum. A flexible sealing list or block 42 is arranged in the groove and may be displaced between end positions defined by the width of the groove 41.

The pressure difference between opposite sides of the flap causes abutment of the sealing list against one of the walls of the groove. The net torque obtained will bring the flap 36 into a sealing abutment against the inside of the housing regardless of the positive or negative pressure difference. The force that is exerted against the housing has a predetermined relation relative the pressure difference and may be determined by the specific shape of the groove.

The conveyor comprising the cassettes 18 is driven from the driven drum 38. In the flaps 36 there are recesses 43 for the joints 20, 20a of the cassettes while the dogs 21 on the cassettes act as dogs and are driven by a respective flap 36 or by members (not shown) attached to the flanges 37 of the drum 38 when the drum is rotated by a driving motor (not shown).

The cassette 18 in FIG. 11 comprises a casing like bottom 45 and a cover 46. Both such units are formed by a network of thin ribs. As material there may be used preferably a temperature resistant plastics material, for instance polyphenylidensulfide (PPS) or polyethensulfon (PES), having in regard the microwave transmission, and the density which preferably should be a density close to the density of water having in regard the best transport conditions. Water is namely the fluid that normally surrounds the cassettes 18 forming the conveyor.

The plastics and the light structure gives a low heat capacity which is of advantage for the heat economy of the process.

The rib construction which at the first sight might seem weak and comprising a bottom (casing) and cover has a plurality of joints 47 arranged at a uniform mutual distance along one side and the entire width of the casing, such that the cover may be turned up to an open position and allow insertion/removal of the product(-s).

The total width of the cassette in FIG. 11 (basically the distance between the joints 20) is thought to correspond to the available treatment width of the heat stabilization system comprising the confinement modules 12, 14. However, the cassettes might be used entirely or partially for one or several portions of a smaller size than said treatment width. In the latter case it is for instance possible to use partition walls between the portions in the cassette, as well as one or several "dummies" instead of real product, said dummies preferably having the same thermic and electric characteristics as the product.

Figure 14:
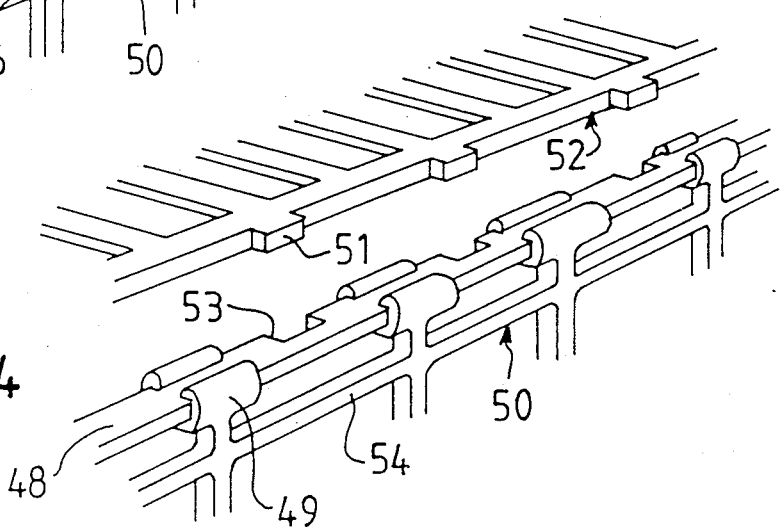
FIG. 14 is a perspective partial view of a cassette having a slider arrangement for locking the cover.

At the opposite side of the casing there are several locking locations 47, at which the cover and the casing are fixed to a rigid and strong unit. In the embodiment according to FIG. 11 there is a slide 48 displaceable crosswise of the cassette and the basic function of which appears from FIG. 14.

The slide 48 is guided in guides 49 on the casing 50. Extensions 51 on the cover 52 are dimensioned to fall into and through cut-outs in the slide when the extensions and the cut-outs are located in register.

By displacing the slide thereafter in the guides 49, the extensions 51 and thereby the cover will be fixed efficiently between the slide and the upper rib 54 of the casing 50.

Figure 12:
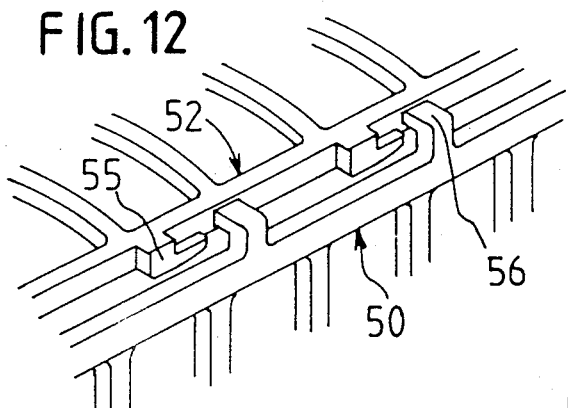
FIG. 12 is a perspective section view of a cassette having a shearable cover and hooks at the cover.

In FIG. 12 there is shown a removable or shearable cover 52 which has hooks 55 for engaging ledges 56 on the casing 50. The shearing of the cover is obtained by a suitable rib structure and a suitable material.

Figure 12A:
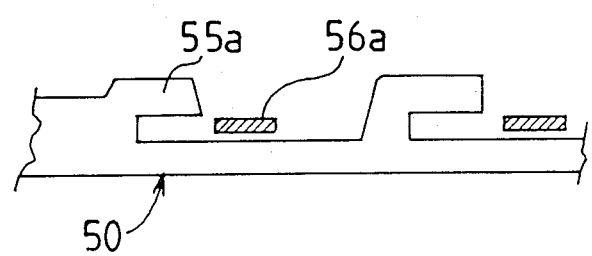
FIG. 12a is a schematic representation of a cassette having a shearable cover and hooks at the casing.

In FIG. 12a there is shown a case being the mirror picture of FIG. 12, where as before the cover is removable or shearable but equipped with locking ledges 56a while the casing has hooks 55a.

Figure 13:
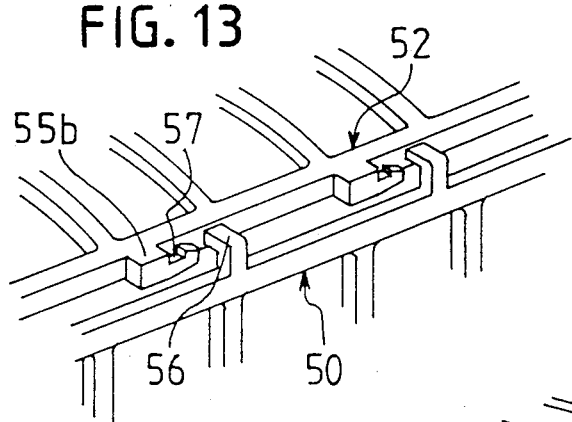
FIG. 13 is a perspective partial section of a cassette having a "double-hook" arrangement on a shearable cover.

In FIG. 13 there is shown a removable or shearable cover provided with double hooks 55b, dimensioned to grip around a substantial portion of the locking ledges by means of the recesses 57. For releasing a cover and a casing in this specific case it is required that the cover is first pressed somewhat downwards before the shearing of the cover is started.

Although the drawings show and the specification describes a limited number of embodiments it is realized that modifications and alternatives are possible within the scope of the invention as defined in the accompanying claims.

We claim:

1. A cassette of a conveyor device for products, preferably food stuff and pharmaceutical compositions, which are to be heat stabilized, the cassette comprising: a thin, and broad-sided casing of substantially uniform thickness having an openable cover, wherein each of said casing and cover comprises a network of thin ribs, said casing and cover being joined by means for joining said casing and cover in a substantially box-like structure for forming said cassette, and wherein the casing and cover are interconnected along one side of the casing at a plurality of joints, such that the casing and the cover which comprise a network of thin ribs form a rigid and strong unit when the cover is closed, and wherein at least one side of the cassette comprises means for pivotal interconnection of other cassettes.

2. A cassette according to claim 1, wherein the cover is removable from the casing and hook elements on the casing are engageable with the cover.

3. A cassette according to claim 1, wherein said cassette has a plurality of locking locations, and further comprises a slider means on said casing for locking the cover at said locking locations.

4. A cassette according to claim 1, wherein said at least one side of the cassette is solid and said means for pivotable connection comprise ears which allow joining of cassettes to a pivotable chain.

5. A cassette according to claim 4, further comprising opposite guide and drive pins arranged on opposing sides of said cassette, to permit the cassette to be guided in guide rails in a conveyor device.

6. A cassette according to claim 1, wherein a plurality of cassettes are pivotably joined together by said pivotable connection means.

7. A cassette according to claim 6, wherein the cassettes are formed from a temperature resistant plastic material density of water.

8. A cassette according to claim 1, wherein said joining means comprise hook-elements on the cover which are engageable with the casing, and wherein the cover is removable from the casing.

9. A cassette according to claim 8, wherein said casing has locking ledges, wherein the hook elements are arranged to grip around said locking ledges of the casing.

10. A cassette according to claim 9, wherein each one of the hook-shaped elements has a recess which surrounds a substantial part of the locking ledge.

* * * * *